United States Patent [19]

Artal

[11] Patent Number: 4,626,214
[45] Date of Patent: Dec. 2, 1986

[54] FIXED DENTAL IMPLANT

[76] Inventor: Alberto A. Artal, Avda. San José, 115-1°F., Zaragoza, Spain

[21] Appl. No.: 609,471

[22] Filed: May 11, 1984

[30] Foreign Application Priority Data

May 17, 1983 [ES] Spain .................................. 272.292
May 3, 1984 [ES] Spain .................................. 279.140

[51] Int. Cl.$^4$ ............................................... A61C 8/00
[52] U.S. Cl. .................................. 433/174; 433/169
[58] Field of Search .............. 433/173, 174, 220, 169

[56] References Cited

U.S. PATENT DOCUMENTS

| | | | |
|---|---|---|---|
| 2,347,567 | 4/1944 | Kresse | 433/174 |
| 2,880,508 | 4/1959 | Lester et al. | 433/169 |
| 3,589,011 | 6/1971 | Sneer | 433/174 |
| 3,618,212 | 11/1971 | Weissman | 433/174 |
| 3,722,094 | 3/1973 | Rivoir | 433/169 |
| 3,955,280 | 5/1976 | Sneer | 433/169 |
| 4,447,210 | 5/1984 | Hidaka | 433/173 |

Primary Examiner—John J. Wilson
Attorney, Agent, or Firm—Darby & Darby

[57] ABSTRACT

A dental implant is disclosed of the type which is fixed to the maxilla of the jaw bone. The implant includes a first elongated body which is externally threaded so that one of its ends can be secured into the maxilla. This body includes an axial bore which extends out of its other end. A second body forming part of the implant includes the artificial tooth at one end and, at the other end, a shaft portion of the first body. The construction permits a certain amount of axial movement between the first and second bodies, once they are fitted together and cushioning is provided between them to simulate the function of a real tooth.

11 Claims, 4 Drawing Figures

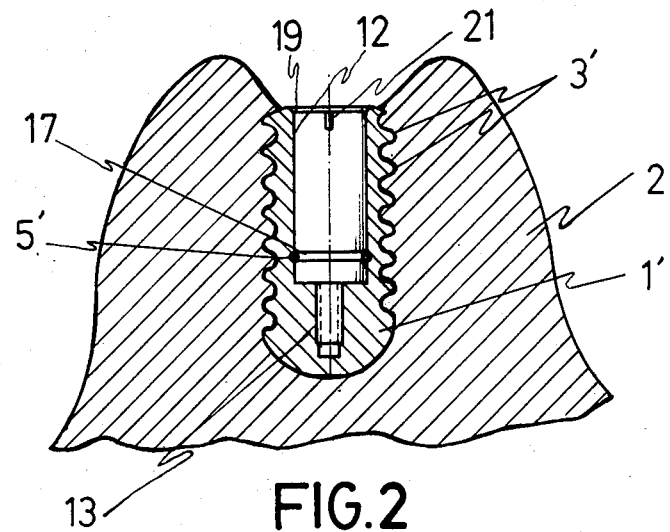
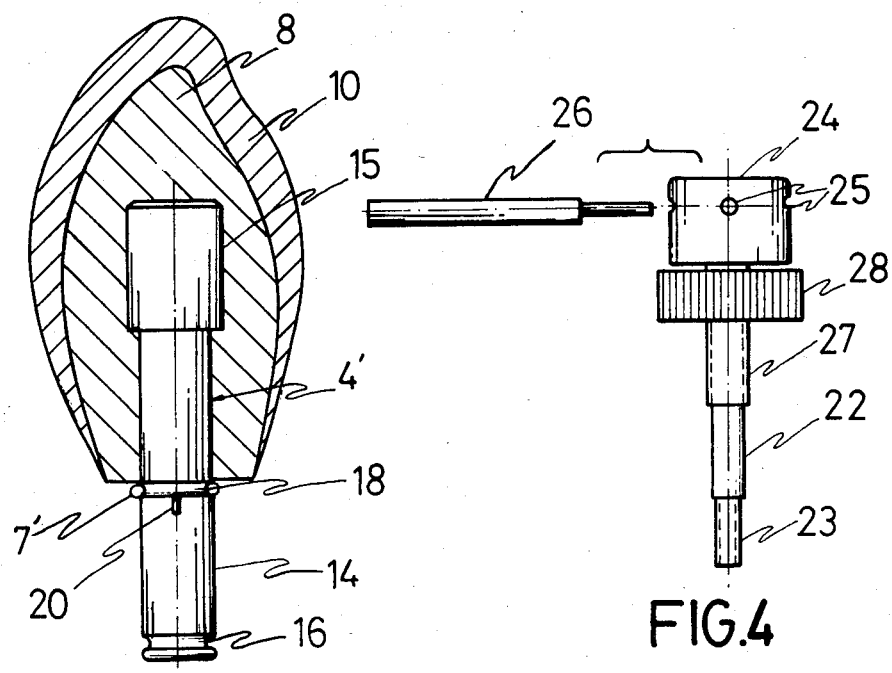

FIXED DENTAL IMPLANT

BACKGROUND OF THE INVENTION

The present invention refers to an improved fixed dental implant.

The dental implant of the invention eliminates the removable prosthesis, being made in a practical and comfortable manner and it is, in turn, aesthetic.

The dental implant of the invention comprises two bodies, one of which is threaded to the maxilla since one of its ends is provided with a thread, while the other body bears the dental prosthesis and is provided with a projecting pin which is inserted in a central axial hole made in the body fixed to the maxilla.

The body bearing the dental prosthesis having a circular section, has annular ridges embedded in the prosthesis, while its cylindrical projecting end is provided with a stepped recess, the dimensions of which correspond with the also stepped axial central hole of the body screwed to the maxilla. Both the front contacting surface between the two bodies as well as the inner slot of the two parts are provided with O-ring seals, the first of which is used as a dampening element and the other furthermore to prevent the separation of both parts, upon being housed between an annular ridge of the body bearing the dental prosthesis and an annular groove made at the corresponding site of the body treaded to the maxilla.

The improvement to the fixed dental implant of the invention resides in proportioning a radial projection at the zone protruding from the body fixed to the dental prosthesis which is introduced in a recess of the zone corresponding to the axial hole of the body fixed to the maxilla, to prevent a possible undesirable turn of both parts. The recess of the projecting pin of the dental prosthesis can have, instead of a small diameter, a constant section; the annular ridges of the end embedded in the dental prosthesis can likewise be replaced by a single one, having a larger diameter than the pin.

BRIEF DESCRIPTION OF THE DRAWING

For a better understanding of this specification, a set of drawings is accompanied, forming an integral part thereof, wherein, illustratively and not limiting, the following is represented:

FIG. 2 is a longitudinal section illustrating another embodiment of the body threaded to the maxilla.

FIG. 3 is a longitudinal view partly in section illustrating a further embodiment of the body constituting the other part of the dental implant.

FIG. 4 illustrates, by way of example, the tool used to insert the body threaded to the maxilla.

DESCRIPTION OF THE PREFERRED EMBODIMENTS

Figure 1:
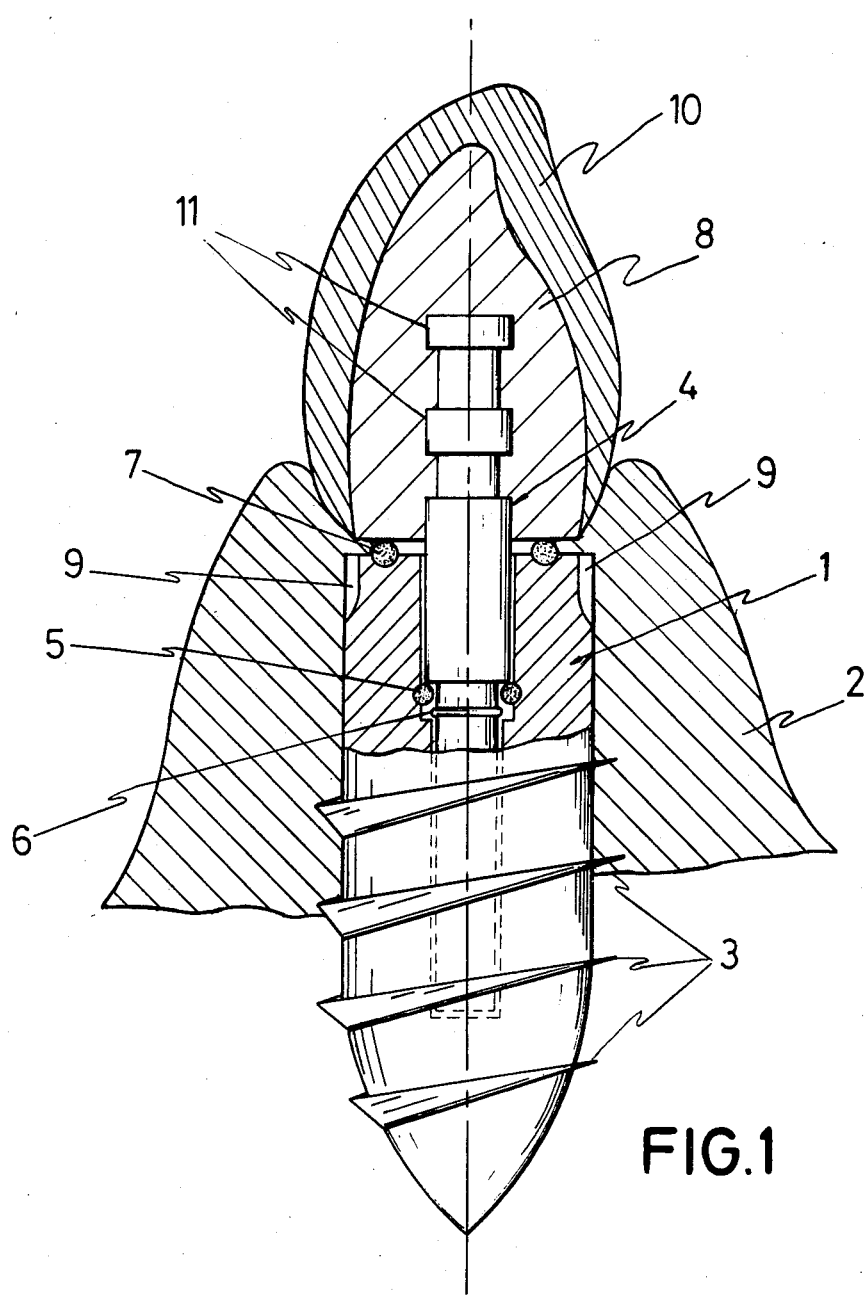
FIG. 1 is a sectional elevation of the dental implant of the invention.

Referring to FIG. 1, the body 1 is threaded to the maxilla 2 by means of a thread 3, mechanically acting as the dental alveola. This body 1 has a central axial hole in which one end of the other body 4 is housed. For the perfect setting thereof and to prevent it from moving out of the former, an O-ring seal 5 has been inserted in the axial hole of the body 1, so that the body 4 drives therein, due to the annular ridges 6 with which it is provided, with a very slight axial movement, as a natural tooth.

The upper base of the body 1 is proportioned with an O-ring seal 7 on which the prosthesis 8 rests, both this seal 7 and the previously mentioned seal 5 having the dual purpose of serving as force-breaker dampeners and guaranteeing a perfect setting of the implant.

At the top and edgewise, according to two orthogonal diameters, the body 1 has notches 9 which aid in the introduction and the extraction thereof. Once the fixed body is set, its extraction will only be necessary in exceptional cases, for example, an accident damaging it or an allergy to the material of which it is made.

Eventually, due to the action of chewing, the cover 10 may be worn out, bu the implant is so constructed that it permits extraction of the active visible part and the reinsertion of a new cover, wherefore it is possible to have fixed teeth indefinitely.

The dental prosthesis 8 is secured to the body 4 by the annular ridges 11 which are embedded therein.

Referring to FIGS. 2 and 3 in which like elements have identical numerals followed by the suffix "prime", the entire side surface of the body 1' constituting one of the independent parts of the dental implant threaded to the maxilla 2, has a thread 3', internally incorporating the axial hole 12 continuing into another 13 having a smaller diameter, this latter being threaded.

In FIG. 3, the cylindrical body 4' to which the dental prosthesis 8 is securely fixed, has the cylindrical pin 14 emerging from the dental prosthesis 8, the end thereof inserted in said pin having a widening 15 embedded therein without the possibility of being separated Fixing between both parts 1' and 3' constituting the dental implant, takes place when the pin 14, emerging from the dental prosthesis 8, is driven into the hole 12 having a larger diameter of the part 1' threaded to the maxilla 2, with the help of an O-ring seal 5 housed in the corresponding annular complementary hollows 16 and 17 made, respectively, in the outer zne of the pin 14 and of the hole 12, at the corresponding position. A second O-ring seal 7 is also disposed in an annular hollow 18 of the pin 14 and in the zone adjacent to the dental prosthesis 8, this O-ring seal 7' being seated on the peripheral recess 19 of the mouth of the threaded part 1'.

When joining the parts 1' and 4' as described, a slight articulation is obtained which permits a short movement of the dental prosthesis 8, in the same way as a natural tooth.

To prevent the dental prosthesis 8 from turning axially with respect to the threaded part 1' set in the maxilla 2, the invention proportions a projection 20, disposed radially to the pin 14, which is made to face a slit 21 made in the threaded part 1', close to the hollow for the O-ring seal 7'.

If the cover 10 of the dental prosthesis 8 is damaged due to an unexpected rough movement, or it is merely worn out due to use, the implant of the invention presents the advantage of permitting extraction of the active visible part and the reinsertion of a new cover, in a completely simple manner.

To facilitate threading of the part 1' to the maxilla 2, a tool, as that represented by way of example in FIG. 4, can be used. Such tool comprises a rod 22 provided at one of its ends with a threading 23 having an identical pitch, as that provided in the part 1' threaded to the maxilla 2, referenced 13. The other end of the rod 22 ends in a head 24 having radial holes 25 to exert the tightening by means of the handle 26. The zone of the rod 22 close to the head 24 has another thread 27 in which the nut 28 is placed, by means of which, once the thread 23 is fixed in the threaded hole 13 of the maxilla 2 when the nut 28 is tightened on the front of the part 1', both elements are blocked, wherefore rotation in one direction or the other can take place.

The bottom outer surface of the part 1' joined to the maxilla 2, has a rounded shape to facilitate introduction; likewise the outer surface of this part 1' has a peripheral bevel to facilitate the slight articulation of the dental prosthesis 8. To prevent any foreign body from being introduced in the holes 12, 13 or groove 14, when the threaded part 1' is set in the maxilla 2, a closure socket, not represented in the drawings, is adjusted to the bevelled surface of the part 1 against which the nut 28 of the insertion tool will butt.

To prevent the relative turn of the two parts of the dental implant, the female part can be provided with an axial hollow having a polygonal section in which the part joined to the prosthesis is adjusted and guided, the rod of which will then have an identical section. In this case, the rod 22 of the insertion tool will likewise have a polygonal section, the lower threaded zone 23 and the nut 28 being eliminated.

I claim:

1. Improved fixed dental implant of the type fixed to the maxilla, comprising a first elongated body having external thread means for securing said first body to the maxilla with one end of said first body extending into the maxilla, said first body having an axial internal bore extending out of the other end thereof, a second elongated body bearing a dental prosthesis at one end and having a shaft portion at the other end dimensioned to be removably received within said bore with a pressure fit, but to be moveable under normal chewing action, a free face on said first body through which said bore extends, an opposing face on said second body positioned to be opposed to said free face when said shaft portion is received in said bore, and sealing means interposed between said free face and said opposing face, said sealing means being made of a sufficiently resilient material so as to serve as a force absorber between said first and second bodies, while also serving as a seal.

2. Improved fixed dental implant according to claim 1, wherein the free face has a groove therein, and the sealing means is constructed to be received in said groove while extending above said free face.

3. Improved fixed dental implant according to claims 1 or 2, wherein the bore has an annular groove spaced from said other end, said shaft portion having an annular recess positioned to be opposite said annular groove when said shaft portion is fully inserted in the bore, said retaining means comprising seal means extending partially into both the annular groove and the annular recess.

4. Improved fixed dental implant according to claim 3, further comprising at least one slit in the bore at the other end of the first body and a radial projection on said shaft portion dimensioned and positioned to be received in said slit, upon full insertion of said shaft portion into said bore, to prevent the relative rotation between said first and second bodies.

5. A dental implant in accordance with claim 3 wherein at least one of said annular recess and said annular groove has a greater axial extent than said seal means, whereby a limited amount of relative axial movement is permitted between said first and second bodies.

6. Improved fixed dental implant according to any one of claims 1 or 2, further comprising at least one slit in the bore at the other end of the first body and a radial projection on said shaft portion dimensioned and positioned to be received in said slit, upon full insertion of said shaft into said bore, to prevent the relative rotation between said first and second bodies.

7. A dental implant in accordance with claim 2 wherein said retaining means includes means for permitting a pre-determined, limited amount of axial movement between said first and second bodies and said sealing means is constructed of a resilient material so as to form a cushion between said first and second bodies.

8. A dental implant in accordance with claim 1 wherein said retaining means includes means for permitting a pre-determined limited amount of axial movement between said first and second bodies.

9. Improved fixed dental implant of the type fixed to the maxilla, comprising a first elongated body having external thread means for securing said first body to the maxilla with one end of said first body extending into the maxilla, said first body having an axial internal bore extending out of the other end thereof, a second elongated body bearing a dental prosthesis at one end and having a shaft portion at the other end dimensioned to be received in said base and retaining means for press-fitting said shaft portion within said bore, the bore having a threaded section of reduced diameter at a distance from said other end and two annular recesses, one close to the reduced diameter section and the other at said other end defining a mouth for said bore; the one end of said first body being rounded off and its other end having a beveled perimeter; the second body having a corresponding complementary annular recess positioned to be opposite said one of the recesses in said first body when said shaft portion is fully received in said bore, and annular seal means extending into said one of the annular recesses in said first body and the corresponding complementary annular recess of said second body, upon the exertion of an insertion pressure of one body in the other.

10. A dental implant in accordance with claim 9 wherein at least one of said one recess in said first body and said complementary recess in said second body has a greater axial extent than said seal means, thereby permitting a limited amount of axial movement between said first and second bodies.

11. Improved fixed dental implant according to claim 9, further comprising at least one slit in the bore at the other end of the first body and a radial projection on said shaft portion dimensioned and positioned to be received in said slit, upon full insertion of said shaft into said bore, to prevent the relative rotation between said first and second bodies.

* * * * *